United States Patent
Clayton et al.

(10) Patent No.: US 6,948,388 B1
(45) Date of Patent: Sep. 27, 2005

(54) WIRELESS REMOTE SENSOR

(75) Inventors: Stanley R. Clayton, Spring Valley, CA (US); Stephen D. Russell, San Diego, CA (US); Mark R. Roser, San Diego, CA (US); Richard L. Waters, San Diego, CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 10/739,751

(22) Filed: Dec. 18, 2003

(51) Int. Cl.⁷ .................. G01K 11/22; G01K 7/00; G01N 25/32
(52) U.S. Cl. .............. 73/862.68; 73/432.1; 73/23.21; 73/31.06; 331/57; 331/65; 257/253; 422/90; 340/634; 324/451; 324/236; 324/71.5
(58) Field of Search .................. 73/23.21, 23.34, 73/31.06, 579, 862.68, 432.1, DIG. 4; 422/90; 324/451, 207.21, 236, 252, 609, 664, 665, 324/71.5; 340/632, 633, 634, 618, 620; 331/57, 331/65, 74; 257/252, 253

(56) References Cited

U.S. PATENT DOCUMENTS

| | | | |
|---|---|---|---|
| 4,227,182 A * | 10/1980 | Ogasawara et al. | 340/870.37 |
| 5,134,371 A * | 7/1992 | Watanabe et al. | 324/252 |
| 5,315,884 A * | 5/1994 | Kronberg | 73/862.68 |
| 5,330,918 A | 7/1994 | Dubbelday | 437/2 |
| 5,642,098 A * | 6/1997 | Santa Maria et al. | 340/618 |
| 5,722,290 A * | 3/1998 | Kronberg | 73/304 C |
| H1744 H | 8/1998 | Clayton | 374/117 |
| 5,895,629 A | 4/1999 | Russell | 422/94 |
| 6,842,078 B2 * | 1/2005 | Manna et al. | 331/57 |
| 2002/0117693 A1 * | 8/2002 | Dodabalapur et al. | 257/253 |
| 2004/0189407 A1 * | 9/2004 | Manna et al. | 331/57 |

FOREIGN PATENT DOCUMENTS

| | | | | | |
|---|---|---|---|---|---|
| EP | 455070 A | * | 11/1991 | | G01D 05/24 |
| JP | 01088146 A | * | 4/1989 | | G01N 27/22 |

* cited by examiner

*Primary Examiner*—Hezron Williams
*Assistant Examiner*—Rose M. Miller
(74) *Attorney, Agent, or Firm*—Peter A. Lipovsky; Michael A. Kagan; Allan Y. Lee

(57) ABSTRACT

A sensing system includes a ring oscillator that emits electromagnetic radiation at a characteristic frequency. The ring oscillator comprises an odd number plurality of inverters that are electrically connected in series. The sensing system also comprises a temperature stabilized voltage source that is used to supply voltage to the inverters of the ring oscillator. A sensing load for sensing a change in a preselected environmental condition is operably connected to the ring oscillator. When the load senses the preselected environmental condition, the sensing load alters the characteristic frequency of the ring oscillator and hence the electromagnetic radiation as emitted by the ring oscillator. A pick-up antenna receives the electromagnetic radiation as emitted by the ring oscillator and detection electronics, operably coupled to the pick-up antenna, measure the frequency of the electromagnetic radiation as received by the pick-up antenna.

14 Claims, 2 Drawing Sheets

WIRELESS REMOTE SENSOR

BACKGROUND

The ensuing description relates generally to sensing systems for detecting environmental changes.

SUMMARY

A sensing system comprises a ring oscillator that has a characteristic frequency and that emits electromagnetic radiation at this characteristic frequency. The ring oscillator comprises an odd number plurality of inverters that are electrically connected in series. The sensing system also comprises a temperature stabilized voltage source that is used to supply voltage to the inverters of the ring oscillator. A sensing load for sensing a change in a preselected environmental condition is operably connected to the ring oscillator. When the load senses the preselected environmental condition, the sensing load alters the characteristic frequency of the—ring oscillator and hence the electromagnetic radiation emitted by the ring oscillator. A pick-up antenna receives the electromagnetic radiation as emitted by the ring oscillator. Detection electronics, operably coupled to the pick-up antenna, measure the frequency of the electromagnetic radiation as received by the pick-up antenna.

Other objects, advantages and new features will become apparent from the following detailed description when considered in conjunction with the accompanied drawings.

Description

Figure 1:
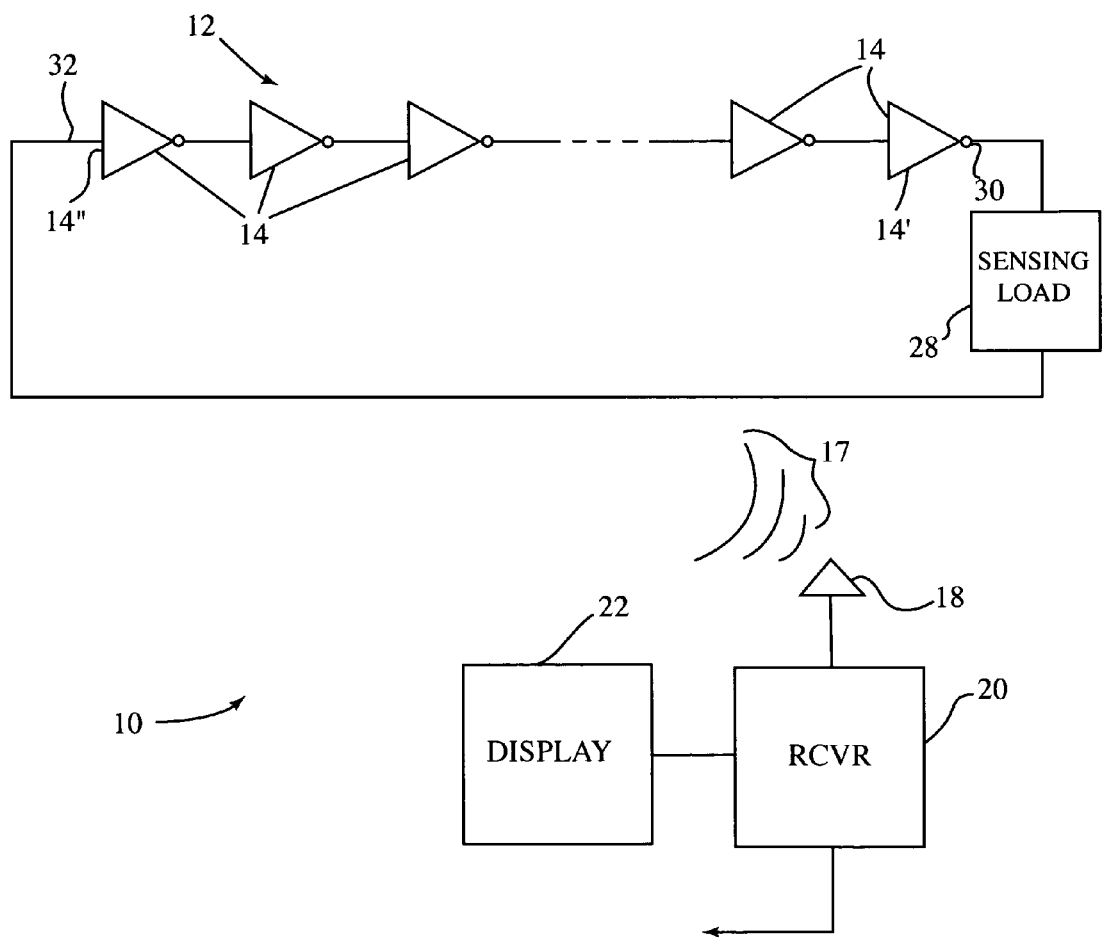
FIG. 1 illustrates a wireless remote sensing scheme.

Referring to FIG. 1, a wireless remote sensing system 10 is shown. System 10 comprises a ring oscillator 12 which in turn comprises an odd number plurality of inverters 14 that are electrically connected in series. Oscillator 12 is any of a wide variety of commercially available oscillators that generates a characteristic frequency w and that emits this frequency as electromagnetic radiation.

Figure 2:
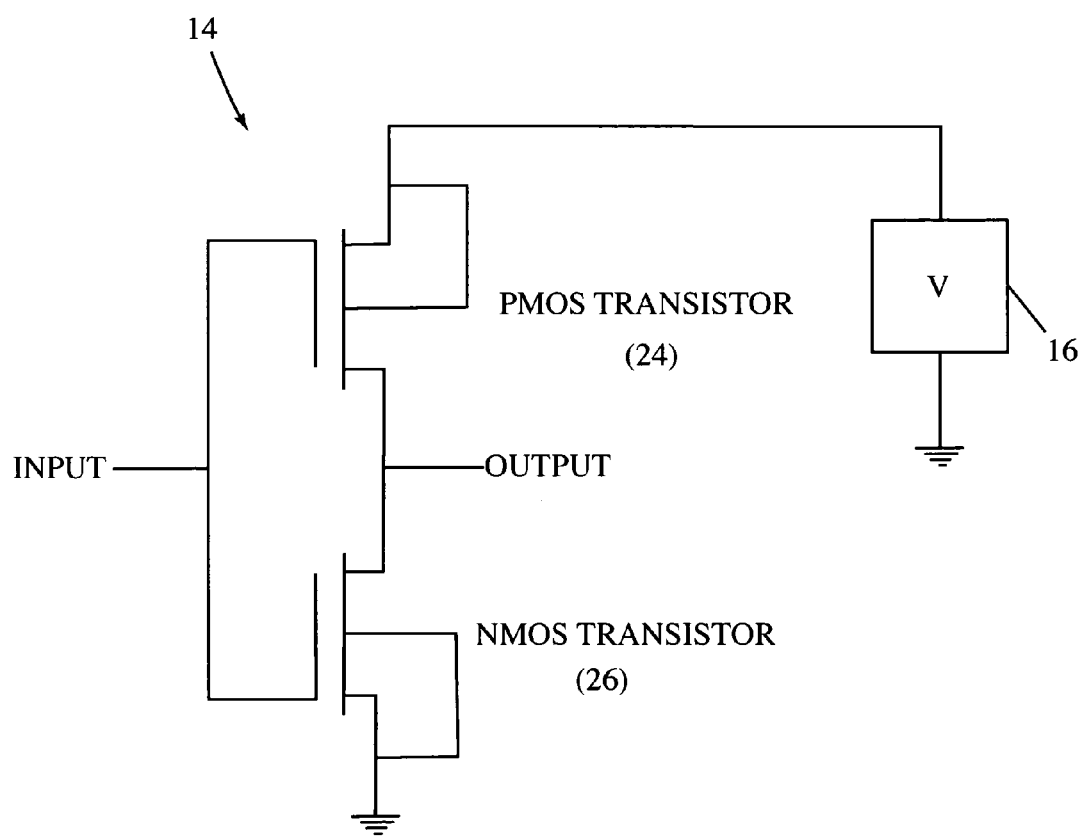
FIG. 2 is a representative inverter.

An example inverter 14 as may be used in oscillator 12 is illustrated in FIG. 2. Inverter 14 takes the form of a typical complementary metal oxide semiconductor (CMOS) inverter. In FIG. 2, a voltage source 16 is shown operably coupled to the inverter. The bias from source 16 causes the inverters of oscillator 12 to change state, leading to an oscillation frequency w that is the characteristic frequency of ring oscillator 12. To provide a temperature stabilized voltage to the inverters of this ring oscillator, voltage source 16 may be a bandgap voltage reference, for example, as is established in the art.

The ring oscillator electromagnetic radiation 17 can be detected by a pick-up antenna 18 located suitably nearby oscillator 12. This antenna does not have to be in direct contact with the oscillator, thereby allowing a remote, non-intrusive, measurement of frequency w. Detection electronics 20, operably coupled to pick-up antenna 18, are used to measure the emitted frequency 17 of ring oscillator 12. The results of detector 20 can be shown on a suitable display 22.

As can be seen in FIG. 2, CMOS inverter 14 includes complementary p and n metal oxide semiconductor field effect transistors (MOSFETs), 24 and 26, respectively. The transistor gate delay is the benchmark of MOSFET operation. It is this gate delay that is altered to provide a sensing attribute to system 10.

Referring again to FIG. 1, there is shown a sensing load 28, whose properties (such as, for example, resistance, capacitance, etc.) change upon a change in a preselected environmental condition being measured. Output 30 of last inverter 14' of serially connected inverters 14 is operably connected to sensing load 28 which is in turn operably connected to an input 32 of first inverter 14" of connected inverters 14.

The characteristic frequency w of ring oscillator 12 is dependent upon the properties of sensing load 28 in series with it. As the condition being measured by sensor load 28 changes, the gate delay time caused by the load will change, thus altering the frequency 17 of the ring oscillator.

The voltage source temperature stabilization circuitry may be employed either on-chip or be coupled to the sensor, thereby allowing higher resolution of frequency changes and concomitant sensor sensitivity. The frequency of the ring oscillator can be easily measured to 1 part in $10^6$ given such stable bias voltage, allowing for precise frequency measurements.

Microelectronic fabrication allows for miniaturization of sensors, permitting the inverters, power source and sensing load to be fabricated as a unit. The wireless remote sensor may also be fabricated monolithically (i.e. on a common substrate) with other circuitry through standard electronic processing.

The sensing load can be changed to detect a variety of parameters. Examples include chemical sensors; biological agent sensors; nuclear sensors; radiological sensors; humidity sensors; liquid sensors; aerosol sensors; electromagnetic sensors; pressure sensors; acceleration sensors; and the like. These sensors can be configured into microelectronic embodiments, and in many cases, monolithically integrated with the ring oscillator and/or associated circuitry.

Microelectronic embodiments of these sensors include charge-sensing field-effect transistor (FET); photodiodes; phototransistors; ion-sensitive field-effect transistors (IS-FETS) whose properties change in response to changes in pH of a solution; platinum (Pt) or palladium (Pd) gated field effect transistors (FETs) known as CHEMFETS whose properties change when is one was exposed to chemical environments; micro electromechanical systems (MEMS) chemical sensors; capacitive MEMS structures; MEMS adsorbate sensors having absorbing surfaces whose properties change when exposed to adsorbates (chemical, biological or physical, for example); MAGFETs whose properties change when exposed to a magnetic field; magnetic MEMS structures; MEMS accelerometers; MEMS optical sensors; MEMS biological agent sensors; and the like.

The ring oscillator of the remote wireless sensor may be fabricated in silicon-on-insulator (SOI) or silicon-on-sapphire (SOS). Since devices fabricated in SOI and SOS have a greater immunity to damage caused by radiation, the sensor could be used in hostile, high radiation, environments such as nuclear reactors, outer space, etc. Furthermore, the insulating substrate provides for the fabrication of passive structures such as inductors or antennas not readily fabricated directly on a semiconductor substrate. Another alternative would be to incorporate an optically powered, on-chip, power source for the ring oscillator (see for example, "A Very High Voltage Silicon-on-Sapphire Photocell Array", U.S. Pat. No. 5,330,918 by W. B. Dubbelday; L. Flesner and G. Imthurn) or radio-isotope power sources that exploit the SOI structure as has been researched by R. L. Shimabukuro and S. D. Russell. Another alternative is to fabricate the ring oscillator in semiconductors selected from group IV semiconductors and their alloys; group III–V semiconductors and their alloys; and group II–VI semiconductors and their alloys.

Obviously, many modifications and variations are possible in light of the above description. It is therefore to be understood that within the scope of the claims the invention may be practiced otherwise than as has been specifically described.

What is claimed is:

1. An apparatus comprising:
    a ring oscillator that emits electromagnetic radiation at a characteristic frequency, wherein said ring oscillator comprises an odd number plurality of inverters electrically connected in series;
    a temperature stabilized voltage source for supplying voltage to said inverters of said ring oscillator; and
    a sensing load for sensing a change in a preselected environmental condition, said sensing load operably connected to said ring oscillator so that when said preselected environmental condition is sensed by said sensing load, said sensing load alters said characteristic frequency of said ring oscillator and thereby alters said electromagnetic radiation emitted by said ring oscillator.

2. The apparatus according to claim 1 further including:
    a pick-up antenna for receiving said electromagnetic radiation as emitted by said ring oscillator; and
    detection electronics operably coupled to said pick-up antenna for measuring the frequency of said electromagnetic radiation as received by said pick-up antenna.

3. The apparatus of claim 1 wherein said sensing load is selected from the following group of sensing loads:
    chemical sensors, biological agent sensors, nuclear sensors, radiological sensors, humidity sensors, liquid sensors, aerosol sensors, electromagnetic sensors, pressure sensors, and acceleration sensors.

4. The apparatus of claim 3 wherein said sensing load is selected from the following group of sensing loads: charge-sensing field-effect transistor (FET); ion-sensitive field-effect transistors (ISFETS); chemical-sensitive field effect transistors (CHEMFETS); photodiode; phototransistor; micro-electro-mechanical systems (MEMS) chemical sensors; capacitive MEMS structures; MEMS adsorbate sensors; magnetic field-effect transistors (MAGFET); magnetic MEMS structures; MEMS accelerometers; MEMS optical sensors; and MEMS biological agent sensors.

5. The apparatus of claim 1 wherein said ring oscillator, said temperature stabilized voltage source and said sensing load are microelectronic elements.

6. A sensor apparatus comprising:
    a ring oscillator having a characteristic gate delay and a characteristic frequency and that emits electromagnetic radiation at said characteristic frequency, wherein said ring oscillator comprises an odd number plurality of inverters electrically connected in series;
    a temperature stabilized voltage source for supplying voltage to said inverters of said ring oscillator; and
    a sensing load for sensing a change in a preselected environmental condition, said sensing load operably connected between an output of a last inverter in said odd number plurality of series connected inverters and an input of a first inverter of said odd number plurality of series connected inverters so that when said preselected environmental condition is sensed by said sensing load, said sensing load alters said gate delay and thereby alters said characteristic frequency of said ring oscillator, thereby altering said electromagnetic radiation emitted by said ring oscillator.

7. The apparatus of claim 6 further including:
    a pick-up antenna for receiving said electromagnetic radiation as emitted by said ring oscillator; and
    detection electronics operably coupled to said pick-up antenna for measuring the frequency of said electromagnetic radiation as received by said pick-up antenna.

8. The apparatus of claim 6 wherein said sensing load is selected from the following group of sensing loads: chemical sensors, biological agent sensors, nuclear sensors, radiological sensors, humidity sensors, liquid sensors, aerosol sensors, electromagnetic sensors, pressure sensors, and acceleration sensors.

9. The apparatus of claim 8 wherein said sensing load is selected from the following group of sensing loads: charge-sensing field-effect transistor (FET); ion-sensitive field-effect transistors (ISFETS); chemical-sensitive field effect transistors (CHEMFETS); photodiode; phototransistor; micro-electro-mechanical systems (MEMS) chemical sensors; capacitive MEMS structures; MEMS adsorbate sensors; magnetic field-effect transistors (MAGFET); magnetic MEMS structures; MEMS accelerometers; MEMS optical sensors; and MEMS biological agent sensors.

10. The apparatus of claim 6 wherein said ring oscillator, said temperature stabilized voltage source and said sensing load are microelectronic elements.

11. A method of detecting a change in an environmental condition comprising:
    providing a ring oscillator having a characteristic gate delay and a characteristic frequency wherein said ring oscillator comprises an odd number plurality of inverters electrically connected in series;
    providing a temperature stabilized voltage source for supplying voltage to said inverters of said ring oscillator;
    providing a sensing load for sensing a change in a preselected environmental condition, said sensing load operably connected between an output of a last inverter in said odd number plurality of series connected inverters and an input of a first inverter of said odd number plurality of series connected inverters, so that when said preselected environmental condition is sensed by said sensing load, said sensing load alters said gate delay and thereby alters said characteristic frequency of said ring oscillator; and
    emitting electromagnetic radiation from said ring oscillator at said characteristic frequency when said preselected environmental condition has not been sensed and emitting electromagnetic radiation from said ring oscillator at a frequency that is altered from said characteristic frequency when said preselected environmental condition is sensed.

12. A method of claim 11 further including:
    providing a pick-up antenna for receiving said electromagnetic radiation as emitted by said ring oscillator; and
    providing detection electronics operably coupled to said pick-up antenna for measuring the frequency of said electromagnetic radiation as emitted by said ring oscillator and as received by said pick-up antenna.

13. The method of claim 11 wherein said sensing load is selected from the following group of sensing loads: chemical sensors, biological agent sensors, nuclear sensors, radiological sensors, humidity sensors, liquid sensors, aerosol sensors, electromagnetic sensors, pressure sensors, and acceleration sensors.

14. The method of claim 13 wherein said sensing load is selected from the following group of sensing loads: charge-sensing field-effect transistor (FET); ion-sensitive field-effect transistors (ISFETS); chemical-sensitive field effect transistors (CHEMFETS); photodiode; phototransistor; micro-electro-mechanical systems (MEMS) chemical sensors; capacitive MEMS structures; MEMS adsorbate sensors; magnetic field-effect transistors (MAGFET); magnetic MEMS structures; MEMS accelerometers; MEMS optical sensors; and MEMS biological agent sensors.

\* \* \* \* \*